United States Patent [19]

Von Esch

[11] 4,087,522
[45] May 2, 1978

[54] AMIDES OF PHOSPHONOACETIC ACID FOR TREATING HERPES SIMPLEX VIRUS TYPE 1 AND 2 INFECTIONS

[75] Inventor: Anne Mary Von Esch, North Chicago, Ill.

[73] Assignee: Abbott Laboratories, North Chicago, Ill.

[21] Appl. No.: 721,611

[22] Filed: Sep. 8, 1976

[51] Int. Cl.² ............................................. A61K 31/66
[52] U.S. Cl. .................................. 424/211; 260/502.5
[58] Field of Search .......................................... 424/211

[56] References Cited
U.S. PATENT DOCUMENTS 3,767,795 10/1973 Schleicher ............................ 424/212

*Primary Examiner*—Jerome D. Goldberg

*Attorney, Agent, or Firm*—Gildo E. Fato; Robert L. Niblack

[57] ABSTRACT

A method of treatng herpes simplex infection in warm-blooded animals by administering to said animals an amide of phosphonoacetic acid of the formula

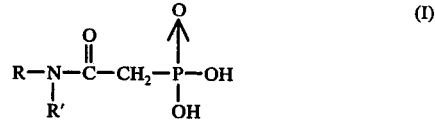

wherein R is $C_2$–$C_{10}$alkyl, $C_3$–$C_8$ cycloalkyl, benzyl, or adamantyl; and R' is H or $C_2$–$C_{10}$alkyl, or its inorganic salts.

9 Claims, No Drawings

AMIDES OF PHOSPHONOACETIC ACID FOR TREATING HERPES SIMPLEX VIRUS TYPE 1 AND 2 INFECTIONS

BACKGROUND OF THE INVENTION

Herpes virus infections, though known, are difficult to treat because of the lack of effective drugs. An effective anti-herpes drug could be used in the treatment or prevention of herpes dermatitis, herpes genitalis, herpes keratitis, herpes encephalitis and as provided by the present invention, herpes simplex virus. Although herpes simplex is a very common, though minor disease, the only basic treatment presently available is the application of 5-iodo-2'-deoxuridine (idoxuridine).

DETAILED DESCRIPTION OF THE INVENTION

This invention relates to a method of treating herpes simplex infections (i.e., types 1 and 2) in warm-blooded animals comprising administering to such infected animals an amide of phosphonoacetic acid of the formula

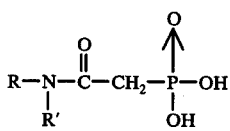

wherein R is $C_2$-$C_{10}$ alkyl, $C_3$-$C_8$ cycloalkyl, benzyl, or adamantyl; and R' is H or $C_2$-$C_{10}$ alkyl, or its inorganic salts.

The amide compounds are active against herpes simplex virus in vivo when administered either as the acid or the alkali metal salts, particularly the sodium and ammonium salts. The compounds are preferably administered topically, but can also be administered orally.

Because the herpes viruses depend for replication upon a unique DNA polymerase independent from the DNA polymerase of the mammalian host, growth of the virus may be stopped by inhibiting this necessary enzyme. These amides of phosphonoacetic acid are potent inhibitors of the enzyme.

The present amides of phosphonoacetic acid (PA) may be prepared by two methods. In the first method, Method (A), monoalkyl (alkylcarbamoylmethyl)phosphonate (as described in co-pending application, U.S. Ser. No. 721,612, now abandoned) is suspended in 25% hydrogen bromide in glacial acetic acid (1 g/10 ml). The mixture is allowed to stand at room temperature overnight and then is concentrated to a viscous oil under reduced pressure. Upon addition of an appropriate solvent, such as methanol, the compound crystallizes. Method A (where R = alkyl and R' = H) is illustrated by the following equation:

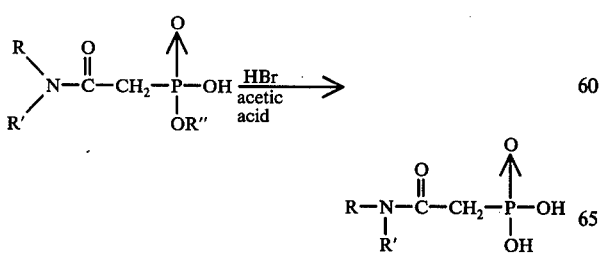

wherein R and R' are as defined above.

In the second method, Method (B), an appropriate amine and dimethyl (carboxymethyl)phosphonate are dissolved in 100 ml. of methylene chloride. As the solution is stirred, dicyclohexylcarbodiimide is added, portionwise. The solution is then stirred overnight and subsequently the dicyclohexylurea is filtered therefrom. Following the filtration, the filtrate is concentrated to a solid, treated with hydrogen bromide in acetic acid and then recrystallized from an appropriate solvent such as methanol. Method (B) is illustrated by the following flow diagram:

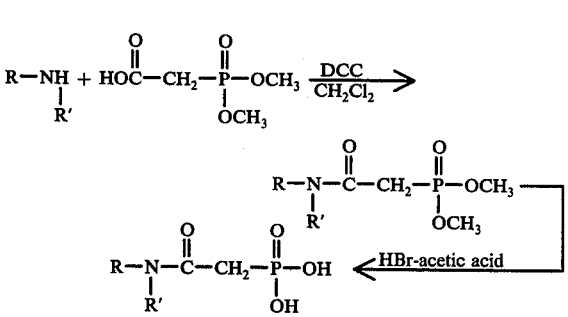

wherein R and R' are as defined above.

The amides of phosphonoacetic acid that may be prepared according to Method (A), as described and illustrated above, include:

II. [(Propylcarbamoyl)methyl]phosphonic acid

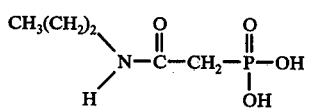

III. [(Butylcarbamoyl)methyl]phosphonic acid

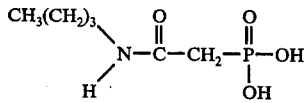

IV. [(Octylcarbamoyl)methyl]phosphonic acid

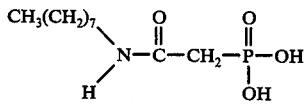

and those that may be prepared according to Method (B), as described and illustrated above, include:

V. [(Cyclohexylcarbamoyl)methyl]phosphonic acid

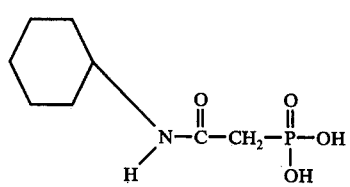

VI. [(Benzylcarbamoyl)methyl]phosphonic acid

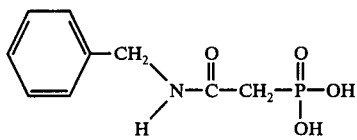

VII. [(t-Butylcarbamoyl)methyl]phosphonic acid

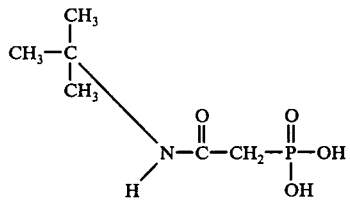

VIII. [(Adamantylcarbamoyl)methyl]phosphonic acid

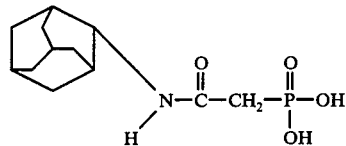

IX. [(Diethylcarbamoyl)methyl]phosphonic acid

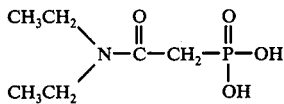

The following examples further illustrate the present invention.

EXAMPLE 1

[(Propylcarbamoyl)methyl]phosphonic acid (II)

1 g. of Monomethyl propylcarbamoylmethylphosphonate was suspended in 10 ml. of hydrogen bromide in glacial acetic acid. The solution was allowed to stand overnight at room temperature. The solution was then concentrated to a viscous oil under reduced pressure. Upon the addition of methanol, the compound crystallized; m.p. 155°–160° C.; yield, 47%.

Analysis Calcd. for $C_5H_{12}NO_4P$: C, 33.15; H, 6.68; N, 7.73; Found: C, 33.36; H, 6.97; N, 7.87.

EXAMPLE 2

[(Butylcarbamoyl)methyl]phosphonic acid (III)

[(Butylcarbamoyl)methyl]phosphonic acid was obtained by using the procedure described in Example 1, above, except monomethyl butylcarbamoylmethylphosphonate was used in place of monopropyl (carbamoylmethyl)phosphonate. m.p. 115°–25° C.; yield, 69%.

Analysis Calcd. for $C_6H_{14}NO_4P$: C, 36.93; H, 7.23; N, 7.18; Found: C, 36.53; H, 7.54; N, 7.42.

EXAMPLE 3

[(Octylcarbamoyl)methyl]phosphonic acid (IV)

The compound, [(octylcarbamoyl)methyl]phosphonic acid was obtained by using the procedure described in Example 1, above, except monomethyl octylcarbamoylmethylphosphonate. The compound was crystallized from 1 N-hydrochloric acid. m.p. 142°–43° C.; yield, 22%.

Analysis Calcd. for $C_{10}H_{22}NO_4P$: C, 47.80; H, 8.82; N, 5.58; Found: C, 47.52; H, 9.00; N, 5.56.

EXAMPLE 4

[(Cyclohexylcarbamoyl)methyl]phosphonic acid (V)

Cyclohexyl amine (0.045 mole) and dimethyl (carboxymethyl)phosphonate (0.04 mole) were dissolved in 100 ml. of methylene chloride. As the solution was stirred, dicyclohexylcarbodiimide (0.045 mole) was added portionwise. The solution was stirred overnight and the mixture filtered. The filtrate was concentrated to a solid and the solid recrystallized from an appropriate solvent such as methanol. m.p. 180°–3° C.; yield 57%.

Analysis Calcd. for $C_8H_{16}NO_4P$: C, 43.47; H, 7.29; N, 6.33; Found: C, 43.19; H, 7.64; N, 6.42.

EXAMPLE 5

[(Benzylcarbamoyl)methyl]phosphonic acid (VI)

Benzylamine (0.045 mole) and dimethyl (carboxymethyl) phosphonate (0.04 mole) were dissolved in 100 ml. of methylene chloride. As the solution was stirred, dicyclohexylcarbodiimide was added portionwise. The solution was stirred overnight, and the mixture filtered. The filtrate was concentrated to a solid and the solid crystallized from an appropriate solvent such as methanol. m.p. 130°–4° C.; yield 76%.

Analysis Calcd. for $C_9H_{12}NO_4P$: C, 47.17; H, 5.20; N, 6.11; Found: C, 47.50; H, 5.59; N, 6.51.

EXAMPLE 6

[(t-Butylcarbamoyl)methyl]phosphonic acid (VII)

Tertiary butyl amine (0.045 mole) and dimethyl (carboxymethyl)phosphonate (0.04 mole) were dissolved in 100 ml. of methylene chloride. As the solution was stirred, dicyclohexylcarbodiimide was added portionwise. The solution was stirred overnight and the mixture filtered. The filtrate was concentrated to a solid. It was recrystallized from an appropriate solvent such as methanol. m.p. 163°–5° C., yield, 61%.

Analysis Calcd. for $C_6H_{14}NO_4P$: C, 35.46; H, 7.25; N, 6.77; Found: C, 35.30; H, 7.04; N, 6.86.

EXAMPLE 7

[(Adamantylcarbamoyl)methyl]phosphonic acid (VIII)

Adamantylamine (0.045 mole) and dimethyl (carboxymethyl)phosphonate (0.04 mole) were dissolved in 100 ml. of methylene chloride. As the solution was stirred, dicyclohexylcarbodiimide was added portionwise. The solution was stirred overnight, and the mixture filtered. The filtrate was concentrated to a solid. It was recrystallized from an appropriate solvent such as methanol. m.p. 190°–4° C.; yield, 32%.

Analysis Calcd. for $C_{12}H_{20}NO_4P$: C, 52.35; H, 8.06; N, 5.09; Found: C, 52.74; H, 7.78; N, 5.09.

EXAMPLE 8

[(Diethylcarbamoyl)methyl]phosphonic acid (IX)

Diethylamine (0.045 mole) and dimethyl (carboxymethyl)phosphonate (0.04 mole) were dissolved in 100 ml. of methylene chloride. As the solution was stirred, dicyclohexylcarbodiimide was added portionwise. The solution was stirred overnight and the mixture was filtered. The filtrate was concentrated to a solid. It was recrystallized from an appropriate solvent such as methanol.

Analysis Calcd. for $C_6H_{14}NO_4P$: C, 36.09; H, 7.23; N, 7.18; Found: C, 36.92; H, 7.53; N, 7.15.

EXAMPLE 9

Herpes Simplex Viruses

Isolation and Purification of Herpes Simplex Type 2 Deoxyribonucleic Acid (DNA) Polymerase Herpes virus infected Wi-38 cells were grown and harvested when 25% of the cells showed cytopathic effect of the virus. The DNA polymerase was isolated according to the procedure of Smith and Gallo (1972) which involved column chromatography on DEAE-cellulose and phosphocellulose. However, buffer containing 20% glyceryl instead of 10% was used. The final enzyme preparation has a specific activity of 313 units/mg. for herpes simplex virus type 2.

Viral Deoxyribonucleic Acid (DNA) Polymerase Assay

The reaction mixture (0.2 ml.) contains 10 μM of 2'-deoxyadenosine-5'-triphosphate, 2'-deoxycytidine-5'-triphosphate, 2'-deoxyguanosine-5'-triphosphate, and 2.5 μM tritium labeled thymidine-5'-triphosphate which was appropriately diluted with unlabeled dTTP to give 880 counts per minute per pico-mole, 10 μg of activated calf thymus DNA, 50 mM Tris-HCl buffer (pH 8.0), 3mM $MgCl_2$, 100 mM KCl and 1 mM dithiothritol. The amounts of enzyme used in each reaction was chosen to give a linear rate for at least 30 minutes at 37° C. The reaction was terminated by the addition of 3 ml. of cold 5% trichloracetic acid — 0.01 M sodium pyrophosphate. The acid-insoluble material was collected, washed twice on glass filter discs (Reeve Angel 984-H) and the incorporated $^3$H-dTMP was determined by a liquid scintillation counter.

The effect of each of the compounds in the inhibition of Herpes simplex type 2 deoxyribonucleic acid (DNA) is recorded below in Table I:

TABLE I

| Compound | Concentration(μg/ml) | Percent Inhibition |
|---|---|---|
| II | >166 | 50% |
| III | 2 | 50% |
| IV | >166 | 50% |
| V | 5.9 | 50% |
| VI | >166 | 50% |
| VII | >166 | 50% |
| VIII | 16.6 | 50% |

EXAMPLE 10

Cutaneous Herpes Test In Mice

Twenty grams, female, CF mice, under light ether anesthesia, had a 20-mm square area of their back plucked free of hair. Herpes virus, type 2, ($10^{7.0}$ $TCID_{50}$/ml) was applied topically (0.05 ml.) to the denuded skin and impregnated into the dermis with a 24-gauge sterile hypodermic needle.

Herpes lesions or vesicles developed in 3 to 5 days. The lesions formed bands which extended over the denuded area. After 10 days the mice developed a paralysis which usually resulted in the death of the animal. The test was allowed to continue for a total of 17 days.

The mice which were treated topically had the phosphonoacetic amide applied to the site of infection as a 2% aqueous suspension two hours after the virus was introduced into the skin, and then twice daily for five consecutive days. The drug was applied a total of 11 times. A single application of a 2% suspension of the phosphonoacetic amide delivered approximately 2 mg. of material. The total dosage to a test mouse was therefore 2 mg. × 11 = 22 mg.

Mice treated orally received the phosphonoacetic amide by gavage. The first medication was administered two hours after the virus was applied to the skin. Medication was continued, twice daily, for six consecutive days. The mice were medicated a total of 11 times during the course of the experiment. The usual dosage was 800 mg./kg./day for a total dosage per mouse of 96 mg.

EFFICACY OF PRESENT DRUGS

The Mann-Whitney "U" Test[1], used to statistically analyze the herpes infection in mice made paired comparisons between the treated and control groups. Only those groups that showed statistically significant differences ($p \leq 0.10$) from the virus control group were labeled "active".

Ranks were evaluated on the basis of severity of infection for each mouse according to a "severity scale" (death, paralysis, lesion) and the time when the sign occurred. The final score of an animal provided his "rank". The time of occurrence of a sign was used to break "ties" in the final score.

The results of the tests are recorded below in Table II.

TABLE II

| | Herpes Test In Mice | |
|---|---|---|
| Compound | Route of Administration | P |
| II | Topical | 0.05 |
| III | Topical | 0.05 |
| IV | Topical | 0.10 |
| | Oral | 0.05 |

[1]Siegel, S. Non-Parametric Statistics for the Behavioral Sciences McGraw Hill (1956) p. 116.

I claim:

1. A method for treating herpes simplex virus types 1 and 2 infections in an animal which comprises administering topically to an animal so infected, a composition containing from 0.2 percent to 10 percent of an amide of phosphonoacetic acid of the formula

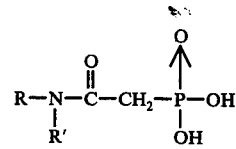

wherein R = $C_2$-$C_{10}$ alkyl, $C_3$-$C_8$ cycloalkyl, benzy, or adamantyl; and R' = H or $C_2$-$C_{10}$ alkyl, or its pharmaceutically acceptable acid addition salts.

2. A method according to claim 1 wherein R is $CH_3(CH_2)_2$ and R' is H.

3. A method according to claim 1 wherein R is $CH_3(CH_2)_3$ and R' is H.

4. A method according to claim 1 wherein R is $CH_3(CH_2)_7$ and R' is H.

5. A method according to claim 1 wherein R is

and R' is H.
6. A method according to claim 1 wherein R is
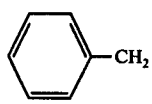
and R' is H.
7. A method according to claim 1 wherein R is
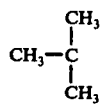
and R' is H.
8. A method according to claim 1 wherein R is
and R' is H.
9. A method according to claim 1 wherein R is $CH_3CH_2$ and R' is $CH_3CH_2$.
* * * * *